United States Patent [19]

Miyoshi et al.

[11] Patent Number: 4,605,735

[45] Date of Patent: Aug. 12, 1986

[54] OLIGONUCLEOTIDE DERIVATIVES

[75] Inventors: Kenichi Miyoshi; Masanori Suzuki; Toru Fuwa, all of Hiroshima, Japan

[73] Assignee: Wakunaga Seiyaku Kabushiki Kaisha, Osaka, Japan

[21] Appl. No.: 578,678

[22] Filed: Feb. 9, 1984

[30] Foreign Application Priority Data

Feb. 14, 1983 [JP] Japan ................................ 58-22516
Apr. 28, 1983 [JP] Japan ................................ 58-75878

[51] Int. Cl.$^4$ ..................... C07H 19/10; C07H 19/20
[52] U.S. Cl. ...................................... 536/27; 536/28; 536/29
[58] Field of Search .......................... 536/27, 28, 29

[56] References Cited

U.S. PATENT DOCUMENTS 4,291,024  9/1981  Turcotte ............................. 536/27
4,476,301 10/1984  Imbach et al. ..................... 536/27

FOREIGN PATENT DOCUMENTS 0063879  6/1982  European Pat. Off. ............... 536/27

OTHER PUBLICATIONS

Shigeko Nishmura et al., Synthetic Nucleosides and Nucleotides, XV.$^{1)}$ 5-dimethylamino-2-oxidoisoquinolin-1yl Diazomethane: A Novel Water-Soluble Fluorescent Labelling Agent for Nucleotides, *Chem. Pharm. Bull.*, Oct. 25, 1979, pp. 1695-1703.
W. J. Smagowicz et al., New Substrate Analogues for RNA Polymerase, *Studia Biophysica*, Berlin, vol. 81, 1980, No. 2/3 pp. 135-136.
Richard I. Gumport et al., T4 RNA ligase as a nucleic acid synthesis and modification reagent, *Nucleac Acids Research*, Symposium Series No. 7, 1980, pp. 167-171.
Pennia R. Langer et al., Enzymatic synthesis of biotin-labeled polynucleotides: Novel nucleic acid affinity probes, *Proc. Natl. Acad Sci. USA*, vol. 78, No. 11, pp. 6633-6637, Nov. 1981.
W. J. Smagowicz et al., Properties of P$^3$ Esters of Nucleoside Triphosphates as Substrates for RNA Polymerase from *Escherichia Coli*, *Biochemistry*, 1981, vol. 20, No. 19, pp. 5538-5546.
R. Bruce Wallace, Hybridization of synthetic oligodeoxyribonucleotides to $\phi\chi$ 174 DNA: the effect of single base pair mismatch, *Nucleic Acids Research*, vol. 6, No. 11, 1979, pp. 3542-3557.
Brenda Connor et al., Detection of Sickle Cell $\beta^s$-goblin allele by hybridization with synthetic oligonucleotides, *Proc. Natl. Acad. Sci. USA*, vol. 80, pp. 278-282, Jan. 1983.
Chemical Abstracts, vol. 94, No. 23, Jun. 8, 1981, p. 241, No. 187647x, Columbus, Ohio, W. J. Smagowicz et al., "New Substrate Analogs for RNA polymerase".
Chemical Abstracts, vol. 96, No. 7, Feb. 15, 1982, p. 207, (a) No. 47771z, P. Langer et al.: "Enzymic Synthesis of Biotin-labeled polynucleotides: novel nucleic acid affinity probes".

*Primary Examiner*—Johnnie R. Brown
*Attorney, Agent, or Firm*—Oblon, Fisher, Spivak, McClelland & Maier

[57] ABSTRACT

Biotin- or 2,4-dinitrophenyl-oligodeoxyribonucleotide derivatve represented by the formula shown below and its preparation method is disclosed:

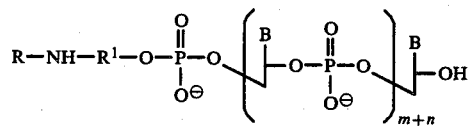

wherein: R is

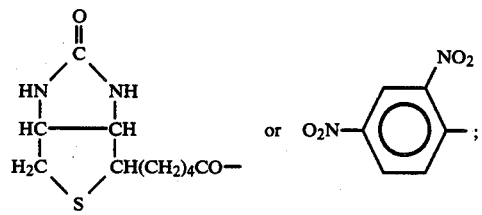

m and n are each 0 or a natural number; R$^1$ is a straight or branched hydrocarbon residue; and B is a base constituting the nucleotide (in which when a plural number of B exist, they may be either identical or different). This compound is useful for use as a nonradioactive affinity probe for nucleic acid or a primer.

5 Claims, 8 Drawing Figures

OLIGONUCLEOTIDE DERIVATIVES

BACKGROUND OF THE INVENTION

1. Technical Field of the Invention

This invention relates generally to oligonucleotide derivatives. More specifically, the present invention relates to an oligonucleotide derivative comprising biotin or 2,4-dinitrobenzene bonded to a moiety other than the base of the nucleotide. The present invention also relates to a method for producing such an oligonucleotide.

2. Description of the Background

Biotin, which is a member of the vitamin B complex and is also called vitamin H, is necessary for the growth of many animals and vegetables. On the other hand, biotin is known to interact potently with avidin in egg white, and this characteristic is put into practical application by utilizing biotin in the form of its derivative such as a biotin-avidin reagent. This is applied as a biochemical reagent for measurement of antigenic density per cell, radioimmunoassay, enzyme immunoassay, etc. Also, a DNA probe having biotin bonded to a nucleic acid has been developed and is now commercially available for diagnosis of infectious and hereditary diseases (Proc. Natl. Acad. Sci. USA, 78, 6633–6637, 1981). The biotin nucleotide derivative in this DNA probe is prepared enzymatically with DNA or RNA as the template by using the biotin derivative of cytidine triphosphate in place of cytidine triphosphate (dCTP).

However, according to our knowledge, a biotin nucleotide derivative thus prepared involves the following problems.

(a) Since biotin is included at the base moiety of the nucleotide, a change occurs in the melting temperature (Tm value) inherent in the oligonucleotide employed.

(b) Synthesis of a cytosine derivative is difficult (in view of the above cited reference).

(c) Synthesis of a DNA having a desired and predetermined base sequence is difficult.

For these reasons, biotin-nucleotide derivatives at the present stage have only a narrow scope of applications and are limited in their usefulness.

Vincent et al have recently developed a DNA probe having 2,4-dinitrophenyl (hereinafter abbreviated as DNP) group bonded to nucleic acid (Nucl. Acids Res., 10, 6787–6796, 1982). They cause a DNP derivative of adenosine triphosphate (ATP) to be incorporated into a DNA strand to be hybridized with a DNA having a complementary base sequence and then detect the objective DNA by adding successively a rabbit antiserum against DNP and peroxide-labelled goat antirabbit $I_gG$. The DNA strand employed here is a fragment taken from nature.

However, according to our knowledge, the DNP-nucleotide derivative thus prepared involves the following problems.

(a) Since DNP is included at the base moiety of the nucleotide, a change occurs in the melting temperature (Tm value) inherent in the oligonucleotide employed.

(b) Synthesis of a DNA having a desired and predetermined base sequence is difficult.

For these reasons, DNP-nucleotide derivatives at the present stage also have only a narrow scope of applications and are limited in their usefulness.

SUMMARY OF THE INVENTION

An object of the present invention is to overcome the drawbacks described above. This invention accomplishes this object by providing an oligonucleotide comprising biotin or 2,4-dinitrobenzene bonded to a specific oligodeoxyribonucleotide at a specific site other than the nucleotide base.

The oligonucleotide derivative according to the present invention comprises an oligodeoxyribonucleotide represented by the formula [VII] set forth below.

The method for preparing the oligonucleotide derivative according to the present invention comprises causing biotin or 2,4-dinitrobenzene to be bonded to the terminal amino group of an oligonucleotide derivative represented by the formula [VI] set forth below to obtain an oligodeoxyribonucleotide represented by the formula [VII] set forth below.

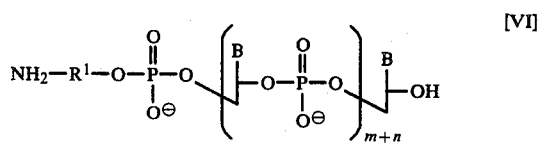

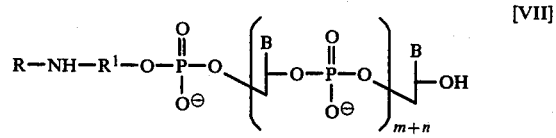

In the above formulae, R is

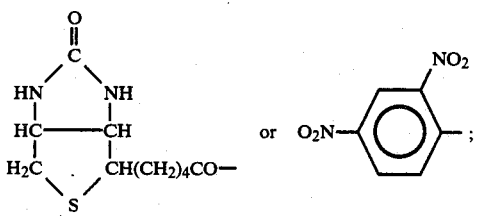

m and n are each 0 or any desired natural number; $R^1$ is a straight or branched hydrocarbon residue; and B is a base constituting the nucleotide. (When a plural number of B exist, they may be either identical or different).

DESCRIPTION OF THE INVENTION

The biotin- or DNP-oligodeoxyribonucleotides synthesized according to the present invention can circumvent the drawbacks of the non-radioactive affinity probe for nucleic acid as described above and have the following advantages.

(a) Since neither biotin nor DNP is included at the base moiety of the nucleotide, it is stable without change in the melting temperature (Tm value).

(b) Synthesis of a biotin- or DNP-oligonucleotide having any base sequence is possible.

(c) A short chain oligomer is sufficient for a probe.

(d) Synthesis is very simple, thus permitting large scale synthesis thereof. Storage for a long term is also possible.

(e) The present oligonucleotide can also be utilized as a primer (DNA fragment in synthesis of template).

Because of such advantages, the present oligonucleotide derivatives may be utilized for a wide scope of applications. More specifically, for example, the biotinor DNP-oligonucleotide may be utilized as a non-radioactive affinity probe for nucleic acids or as a primer as described above, and its detection may be performed according to various methods such as sedimentation by an antibody, activity assay of an enzyme, visualization with an affinity column fluorochrome, etc. Furthermore, the oligonucleotide derivative of the present invention is advantageous with respect to the risk of exposure, cost, disposal of the waste and storability, as compared with the radioactive probe ($^{32}P$).

In addition, the DNP group can easily be detected with a commercially available rabbit antiserum (e.g., Code No. 61-006-1, produced by Miles Laboratories) or a monoclonal antibody against DNP.

DETAILED DESCRIPTION OF THE INVENTION

Oligonucleotide Derivative [VII]

The oligonucleotide derivative according to the present invention is represented by the formula [VII] as described above.

In the above formula, the symbol

is conventionally used for showing the deoxyribonucleoside residue after removal of 3'- and 5'-hydroxyl groups from 2'-deoxyribonucleoside, and has specifically the structure shown below:

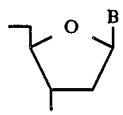

The substituent B represents a base constituting the nucleotide and is usually adenine, thymine, cytosine or guanine. When a plural number of B exist in the compound [VII], they may be the same or different.

Each of m and n is 0 or a natural number. The polymerization degree of the oligonucleotide derivative of the present invention is represented in terms of m+n because the fractions with polymerization degrees of m and n, respectively, are condensed according to a preferred preparation method in the present invention (as hereinafter described in detail). In this case, m may practically be 0 to 6, particularly 1 to 4, and n may practically be 0 to 40, particularly 0 to 20.

The group $R^1$ is a divalent straight or branched hydrocarbon residue for coupling the nucleic acid moiety of the compound [VII] with the biotin or DNP moiety. This may suitably be a straight or branched alkylene group, particularly having about 2 to 20 carbon atoms. Preferably, $R^1$ is an alkylene group having 2 to 6 carbon atoms, a straight $C_2$–$C_6$ alkylene being more preferable.

Synthesis of the Compound [VII]

The oligonucleotide derivative of formula VII according to the present invention can be synthesized according to any desired method suited for the purpose.

A preferable method comprises causing biotin or 2,4-dinitrobenzene to be bonded to the amino group of an oligonucleotide derivative of the above formula [VI], namely, a compound in which a primary amino group has been introduced through the group $R^1$ into an oligodeoxynucleotide at its 5'-terminal phosphate group.

On the other hand, the compound of the formula [VI] can be synthesized according to the method which comprises synthesizing an oligonucleotide and introducing a primary amino group into the oligonucleotide formed so as to be extended from the 5'-hydroxyl group.

Figure 1:
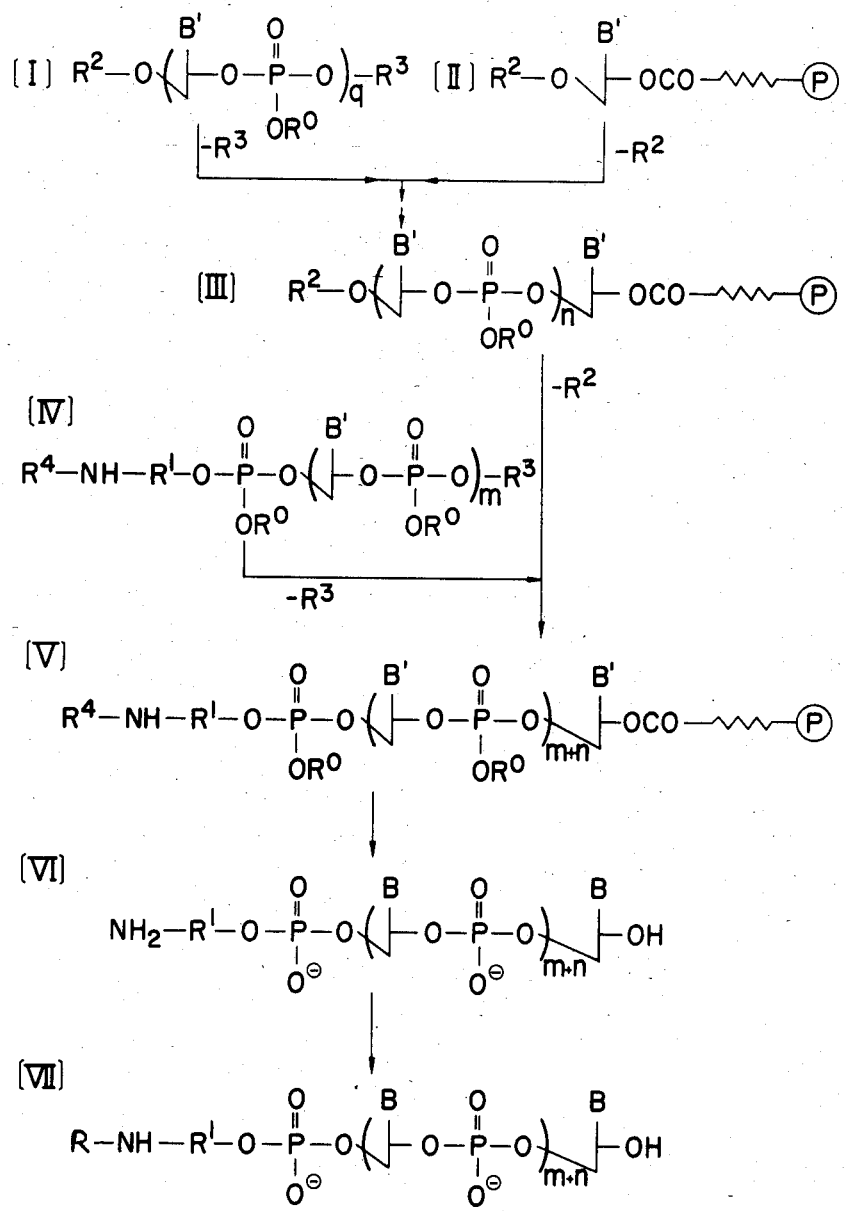
FIG. 1 is a flow chart indicating an example of the method for synthesis of the compound of the present invention in Examples 1 and 2 set forth hereinafter.

FIG. 1 shows a flow chart illustrating an example of the preferable synthetic method. The symbols in the flow chart have the meanings defined below (their significances or details being as described hereinafter).

$R^0$: a substituent for protection of a phosphoryl group, o-chlorophenyl group being generally used;

$R^1$: divalent hydrocarbon residue;

$R^2$: a protective group for 5'-terminal hydroxyl group, dimethoxytrityl group being generally used;

$R^3$: a substituent which can easily be eliminated under the conditions under which all other protecting groups are stable to produce a phosphodiester, a cyanoethyl group being generally used;

$R^4$: a protecting group for amino group, trifluoroacetyl group being generally used;

q: any desired natural number smaller than n;

m: 0 or any desired natural number;

n: 0 or any desired natural number;

B: a base;

B': a protected base, generally selected from $N^6$-benzoyladenine, N-isobutyrylguanine, $N^6$-benzoylcytosine and thymine (i.e., no protection needed);

Ⓟ: carrier through a spacer, usually one as shown below:

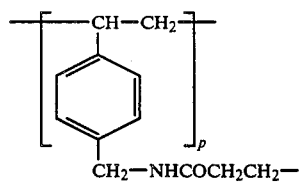

(wherein p is polymerization degree of styrene)

R:

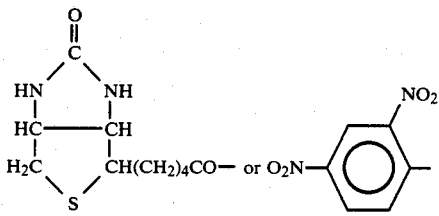

Synthesis of the Compound [VI]

Generally speaking, the methods for synthesis of oligonucleotides are the triester method and the phosphite method, each involving the solid phase method and the liquid phase method. We have already established a technique for producing oligonucleotides according to the solid phase phosphotriester method. Our methods as disclosed in the references set forth below are preferred for synthesis of the compound [VI].

Tetrahedron Letters 1979, 3635 (1979)
Nucleic Acids Research 8, 5473 (1980)
Nucleic Acids Research 8, 5491 (1980)
Nucleic Acids Research 8, 5507 (1980)
Nucleic Acids Research Symposium Series 7, 281 (1980)

As a method for introducing a primary amino group into the 5'-hydroxyl group of the oligonucleotide as synthesized above through a phosphate group, that is, as a method for synthesizing the compound [VI], there is our method as disclosed in Japanese Patent Application No. 138136/1982.

The method of synthesizing the compound [VI] according to an embodiment thereof is described below. As shown in FIG. 1, the derivative of the compound [I] from which the protecting group $R^3$ has been removed and the derivative of the compound [II] from which the protecting group $R^2$ has been removed are condensed, and these operations are repeated to synthesize the compound [III]. The method of synthesizing an oligonucleotide compound [III] is known in the art as mentioned above.

On the other hand, the compound of the formula [IV] is synthesized according to our method (reference: Japanese Patent Application No. 138136/1982). More specifically, $R^2$ of the compound [I] is removed to form a 5'-hydroxyl compound, which is caused to react with a phosphorylating agent (e.g., phosphoditriazolide, phosphodichloride or phosphodibenzotriazolide) to be phosphorylated and then condensed with an amino alcohol compound of which amino group is protected, namely, $R^2$—NH—$R^1$—OH [which compound can be obtained by protecting the amino group of an omega-aminoalcohol (NH$_2$—$R^1$—OH) with $R^2$], whereby the compound [IV] can be obtained (reference: the specification of the above patent application for its details).

The compound [IV] after removal of the protecting group $R^3$ therefrom is condensed with the compound [III] from which the protecting group $R^2$ has been removed to synthesize the compound [V]. Condensation may be carried out according to a method which is substantially the same as that for the condensation in the synthesis of the compound [III].

By removing all of the protecting groups on the compound [V] thus synthesized, the compound [VI] can be obtained. The protecting group CO~~~Ⓟ, o-chlorophenyl group and the acyl group in the base moiety can be removed by treatment with a 0.5M tetramethylguanidine-pyridine-2-carboaldoxime in dioxane-water (9:1, v/v) solution, followed by alkali treatment (conc. ammonia water). In the case where $R^4$ is trifluoroacetyl group, it can be removed at the same time by treatment with ammonia, but treatment with mercaptoethanol is required in the case where $R^4$ is o-nitrophenylsulfenyl group. When another group is employed for $R^4$, still another treatment may be applicable under the conditions where the oligonucleotide moiety is stable. In this context, various methods have already been known for synthesis of deoxyoligoribonucleotide, and as to details concerning the kinds of protecting groups, introduction or removal thereof and condensation other than those as mentioned above, reference may be made to textbooks or review publications, for example, "Synthesis of Nucleosides and Nucleotides" (Maruzen, Japan, 1977), "Organic Chemistry of Nucleic Acids" (Kagaku Dojin, Japan, 1979), "Nucleic Acid" (Asakura Shoten, Japan, 1979), Tetrahedron, 34, 3143 (1978), Journal of the Society of Organic Synthetic Chemistry, Japan, 34, 723 (1978) and "Kagaku no Ryoiki" (Domain of Chemistry) 33, 566 (1979).

Synthesis of the Compound [VII]

The oligodeoxyribonucleotide (the compound [VII]) can be prepared by bonding biotin or 2,4-dinitrobenzene to the primary amino group extended from the 5'-terminal of the above compound [VI].

(1) Reaction with biotin:

Bonding between the two compounds can be carried out according to any method which can realize formation of an amide bonding through dehydration between the carboxyl group of biotin and the amino group of the compound [VI]. When an amino group or a hydroxyl group which can react with the carboxyl group of biotin exists in the compound [VI], the reaction can be carried out under appropriate protection of such groups. Thus, the expression "by bonding biotin to the terminal amino group of the oligonucleotide derivative represented by the formula [VI], the biotin-oligonucleotide represented by the formula [VII] is obtained" is also inclusive of the case where the compound [VI] is protected as described above. Further, this expression is also inclusive of the case where biotin is in the form of its functional derivative. Specific examples of functional derivatives of biotin are its acid halides and active esters.

A preferable method for obtaining bonding between the amino group and biotin in this sense comprises a reaction between the amino group of the oligonucleotide derivative and an active ester of biotin. An active ester of biotin is preferred because it can react selectively only with the primary amino group extended from the 5'-terminal hydroxyl group without undergoing reaction with the amino group at the base moiety of the oligonucleotide and also because the reaction operation is simple. An "active ester of biotin" means a biotin derivative having an ester bonding which can readily react with other functional groups (usually amino groups), typically succinimide-, p-nitrophenyl-, benzotriazolide- and 2,4,5-trichlorophenyl-ester.

Another preferable method for causing bonding between the amino group and biotin comprises carrying out bonding of both in the presence of a condensing agent. Examples of suitable condensing agents are dicyclocarbodiimide, carbonylimidazole, and Woodward reagent "K".

According to any of these methods, the reaction method can be any one suited for the purpose. The specific reaction method for a given reaction system is suitably determined by referring to the experimental examples as given below and various textbooks such as "Peptide Synthesis" (Maruzen, Japan 1975) and "Chemistry of Proteins IV" (1977).

(2) Reaction with 2,4-dinitrobenzene:

The DNP-oligodeoxyribonucleotide (the compound [VII]) can be obtained by causing 2,4-dinitrobenzene to be bonded to the primary amino group extended from the 5'-terminal of the above compound [VI].

Bonding between these compounds can be accomplished according to any desired method which can realize formation of C—N bonding between the 1-position of 2,4-dinitrobenzene and the amino group of the compound [VI].

Bonding between the two compounds is generally accomplished through condensation with H-X elimination between the derivative of the former, namely DNP-X (where X is a 1-substituent) and the amino group. X is preferably a halogen. The derivative wherein X is a halogen, namely, 1-halogeno-2,4-dinitrobenzene is preferred because it can react selectively only with the primary amino group extended from the terminal 5'-hydroxyl group without undergoing the reaction with the amino group at the base moiety of the oligonucleotide. Above all, 1-fluoro-2,4-dinitrobenzene is readily available commercially, and the reaction with the amino group of the compound [VI] can proceed under mild reaction conditions.

The reaction of a 1-halogeno-2,4-dinitrobenzene with the compound [VI] can be practiced in a homogeneous solution (the solvent being, for example, a water-containing alcohol) or a heterogeneous solution (the solvent being, for example, water) of the two compounds at a temperature of the order of 10° to 50° C. in the presence of an agent for capturing a hydrogen halide liberated (e.g., sodium hydrogen carbonate, triethylamine, and potassium hydroxide). The desired product may be recovered by, for example, extraction. As to incorporation of DNP, reference may be made to an appropriate review publication, for example, "Course of Chemical Experiments 1, Chemistry of Proteins II, p.118" (published by Maruzen Co., 1976).

EXPERIMENTAL EXAMPLES

Example 1 (Preparation of Biotin-oligonucleotide)

Figure 2:
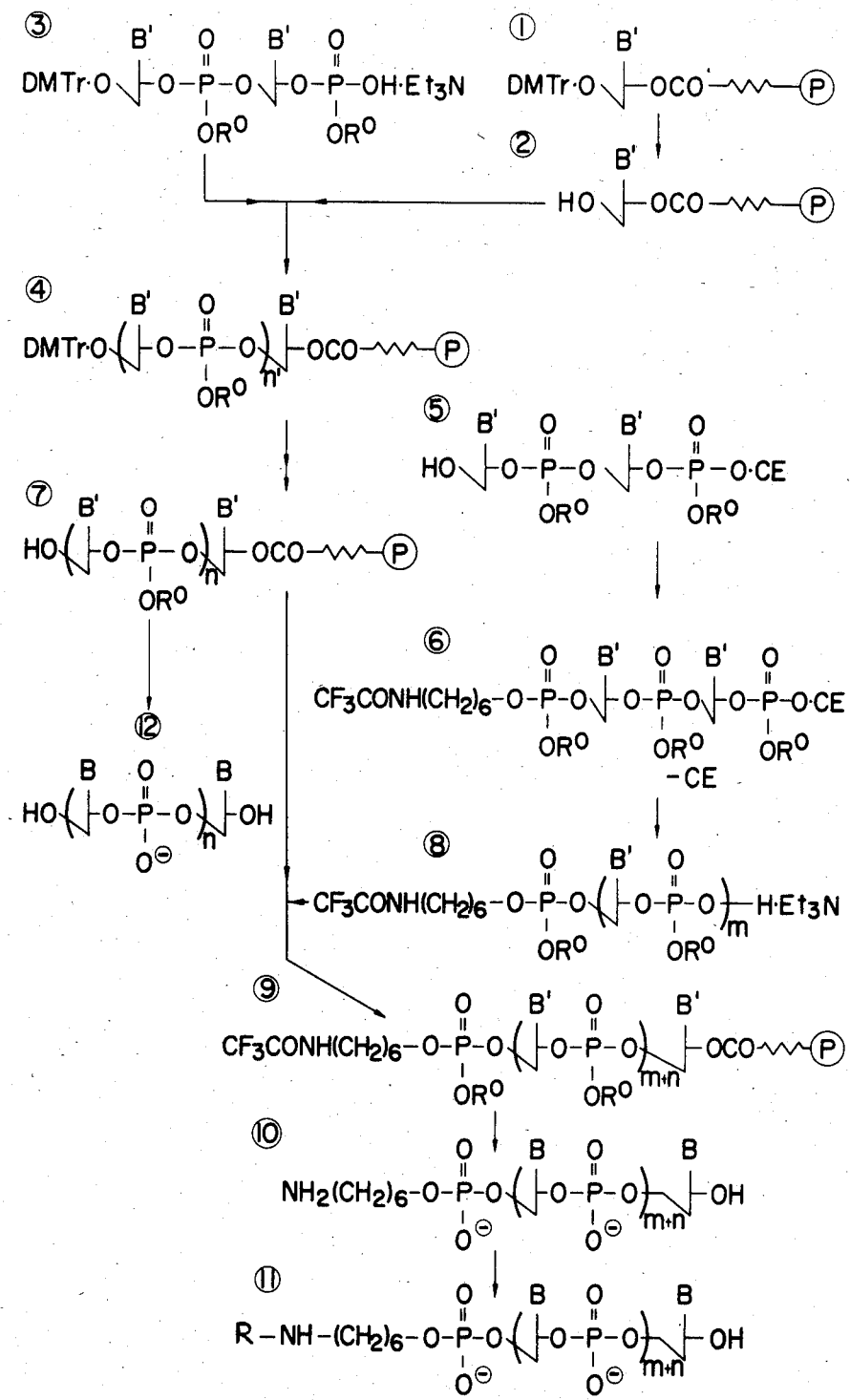
FIG. 2 is a flow chart of the method for synthesis of the compound of the present invention as illustrated in the Experiments in Examples 1 and 2.

Flow chart:

The compound of the present invention (the compound ⑪ in FIG. 2) was prepared according to the flow chart shown in FIG. 2.

In FIG. 2, the symbols have the following meanings.
B': N-Benzoyl-adenine
B: adenine
DMTr: dimethoxytrityl
P :

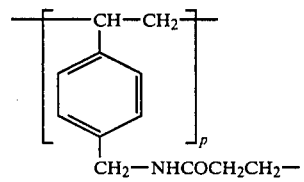

(p: degree of polymerization)
$R^0$: o-chlorophenyl
Et: ethyl
CE: cyanoethyl
m: 2
n': 2
n: 12
R:

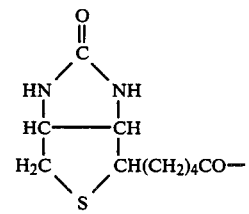

Synthesis Of The Compound [VI]

Experiment 1-1

Dimethoxytrityladenosine/resin [①] (resin is merely a carrier, but since the desired compound carried on a resin is substantially the same in appearance as the resin itself, the compound carried on a resin is hereinafter called merely resin) in a quantity of 300 mg (0.033 mmol), was washed three times with 10 ml of an isopropanol-methylene chloride (15:85, v/v) solution, and then the reaction (detritylation) was carried out four times each for 5 minutes with 8 ml of a 1.0M zinc bromide in an isopropanol-methylene chloride solution to obtain a resin [②]. The resin [②] was washed three times with 10 ml of an isopropanol-methylene chloride solution, and after addition thereto of a solution of 150 mg of the dinucleotide [③] in pyridine, the mixture was subjected to azeotropic distillation to make the system anhydrous. Then, 150 mg (0.5 mmol) of mesitylenesulfonyl nitrotriazolide (hereinafter abbreviated MSNT) and 2 ml of anhydrous pyridine were added to the system, and the reaction (condensation) was carried out for 90 minutes. After the reaction, the reaction mixture was washed three times with 10 ml of pyridine, and 10 ml of a solution containing a catalytic amount (about 10 mg) of dimethylaminopyridine (hereinafter abbreviated DMAP) in acetic anhydride-pyridine (1:9, v/v) to carry out the reaction for 10 minutes, thereby protecting or masking the unreacted 5'-hydroxyl group through acetylation. The protected compound was washed with pyridine to obtain the compound [④'] (n=2). The above operation was repeated 6 times to obtain the compound [④] (n=12).

On the other hand, the reaction between 800 mg (0.71 mmol) 5'-hydroxy-dinucleotide [⑤] and o-chlorophenyl phosphoditriazolide was carried out in a solution of the latter in dioxane (1.0 mmol, 6 ml) for 2 hours, followed further by the reaction continued for 2 hours with addition of 300 mg (1.4 mmol) of trifluoroacetyl-6-aminohexanol and 115 mg (1.4 mmol) of 1-methylimidazole. After completion of the reaction, the solvent was evaporated, and the residue was dissolved in chloroform. Then, the solution was washed with water, a 0.5M aqueous sodium dihydrogen phosphate solution, a saturated aqueous sodium hydrogen carbonate solution and an aqueous 5% sodium chloride solution, respectively, and dried over anhydrous sodium sulfate. The chloroform layer was concentrated and purified on a silica gel column, eluting with chloroform containing 0 to 4% methanol. The eluate was concentrated and added dropwise into pentane to obtain a powdery compound [(6)].

To the compound [(7)] obtained by detritylation of 115 mg (3.45 μmol) the compound as prepared above [ 4 ] (n=12) according to the same procedure as described above was added the compound [(6)] (0.04 mmol) which had been decyanoethylated by treatment thereof with 3 ml of a triethylamine-pyridine-water (1:3:1, v/v) solution. After the system was made anhydrous, 50 mg (0.2 mmol) of MSNT and 1 ml of pyridine were added thereto, and the reaction (condensation) was carried out for 90 minutes. After completion of the reaction, the product was washed with pyridine and methanol and dried to obtain a completely protected oligonucleotide derivatives [(9)].

15 mg of the oligonucleotide derivative [(9)] was added to 200 μl of a solution of 0.5M tetramethylguanidine-pyridine-2-carboaldoximate in dioxane-water (9:1, v/v), and reaction was carried out in a centrifugal precipitating tube at room temperature for 24 hours. After the reaction, conc. ammonia water (2.5 ml) was added thereto, and, with the vessel in sealed state, the reaction was carried out at 50° C. overnight. After completion of the reaction, the mixture was filtered, and the filtrate was concentrated. The concentrate was dissolved in water and washed with ether. The aqueous layer was concentrated and purified by desalting on Sephadex G-50 (φ1.5×120 cm, eluting with 0.05M triethylammonium bicarbonate buffer, pH 7.5) to obtain a pendadecadenylic acid derivative [(10)].

According to similar procedures, the oligonucleotide derivatives of Experiments 1-2, 1-3 and 1-4 were prepared. The compounds as synthesized above are shown in Table 1.

TABLE 1

| | | Derivative Identities of Compound (10) |
|---|---|---|
| Experiment | m + n | $(B)_{m+n}B$ |
| 1-1 | 14 | A A A A A A A A A A A A A A |
| 1-2 | 14 | T T T T T T T T T T T T T T |
| 1-3 | 14 | G G A T G C A T C A C C A C C |
| 1-4 | 16 | A A T C T G G T G A G A A G C G C |

In the above Table, A represents adenine, T thymine, G guanine and C cytosine.

Figure 3:
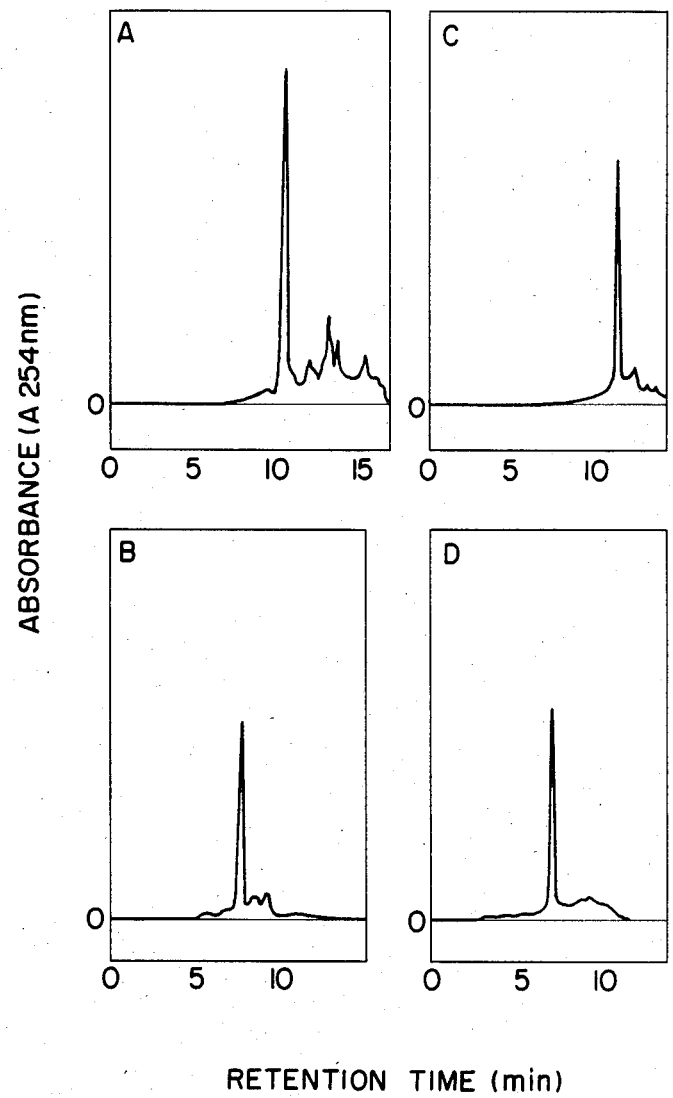
FIGS. 3A through 3D are chromatograms indicating the results of the high speed liquid chromatography of the compounds [VI] as illustrated in the Experiments in Examples 1 and 2.

The results of high-speed liquid chromatography for these four types of compounds are shown in FIG. 3, in which A through D are charts for the compounds of Experiments 1-1 through 1-4, respectively.

Preparation of Biotin-pentadecaadenylic Acid [(11)]

Experiment 2-1

About 1.0 OD of the pentadecaadenylic acid derivative [ 10 ] as prepared in the above experiment 1-1 was dissolved in 10 μl of 0.1M an aqueous sodium hydrogen carbonate solution (pH 8.3) and, with addition of 10 μl of a solution of biotin succinimide ester in dimethylformamide (corresponding to some hundred-fold excess), the reaction was carried out at 4° C. overnight or at room temperature for 4 hours to synthesize biotin-pentadecaadenylic acid [(11)].

The reaction was monitored by high-speed liquid chromatography and 20% polyacrylamide gel electrophoresis.

The same operation as in Experiment 2-1 was also applied for the compounds [(10)] prepared in the above Experiments 1-2, 1-3 and 1-4, respectively, to prepare the respective compounds [(11)]. The experiments conducted here are called Experiments 2-2, 2-3 and 2-4, respectively. The compounds prepared in Experiments 2 are shown in Table 2.

TABLE 2

| | | Derivative Identities of Compound (11) |
|---|---|---|
| Experiment | m + n | $(B)_{m+n}B$ |
| 2-1 | 14 | A A A A A A A A A A A A A A |
| 2-2 | 14 | T T T T T T T T T T T T T T |
| 2-3 | 14 | G G A T G C A T C A C C A C C |
| 2-4 | 16 | A A T C T G G T G A G A A G C G C |

In the above Table, A represents adenine, T thymine, G guanine and C cytosine.

Reference Experiment 3

For the purpose of comparison with respect to reactivity, the compounds [(12)] having 5'-hydroxyl group obtained through deprotection of the oligonucleotides [(7)] as synthesized above Experiments 1 were also similarly caused to react with biotin succinimide ester.

The reference experiments are called Experiments 3-1, 3-2, 3-3, 3-4, respectively. The compounds used in Experiments 3 are shown in Table 3.

TABLE 3

| | | Derivative Identities of Compound (12) |
|---|---|---|
| Experiment | n | $(B)_nB$ |
| 3-1 | 12 | A A A A A A A A A A A A |
| 3-2 | 12 | T T T T T T T T T T T T |
| 3-3 | 12 | A T G C A T C A C C A C C |
| 3-4 | 14 | T C T G G T G A G A A G C G C |

In the above Table, A represents adenine, T thymine, G guanine and C cytosine.

Figure 4:
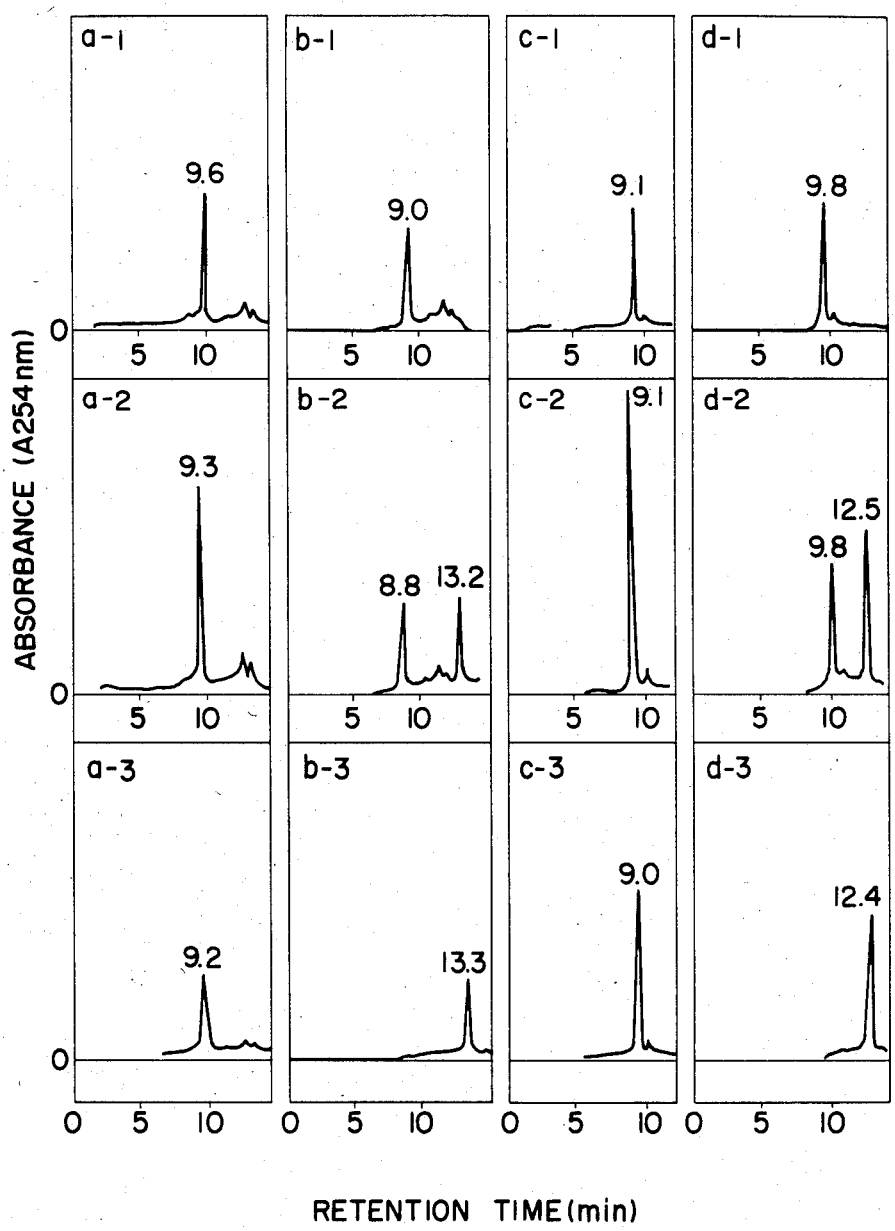
FIGS. 4 and 5 are charts showing elution patterns of the high speed liquid chromatography in Example 1.
Figure 5:
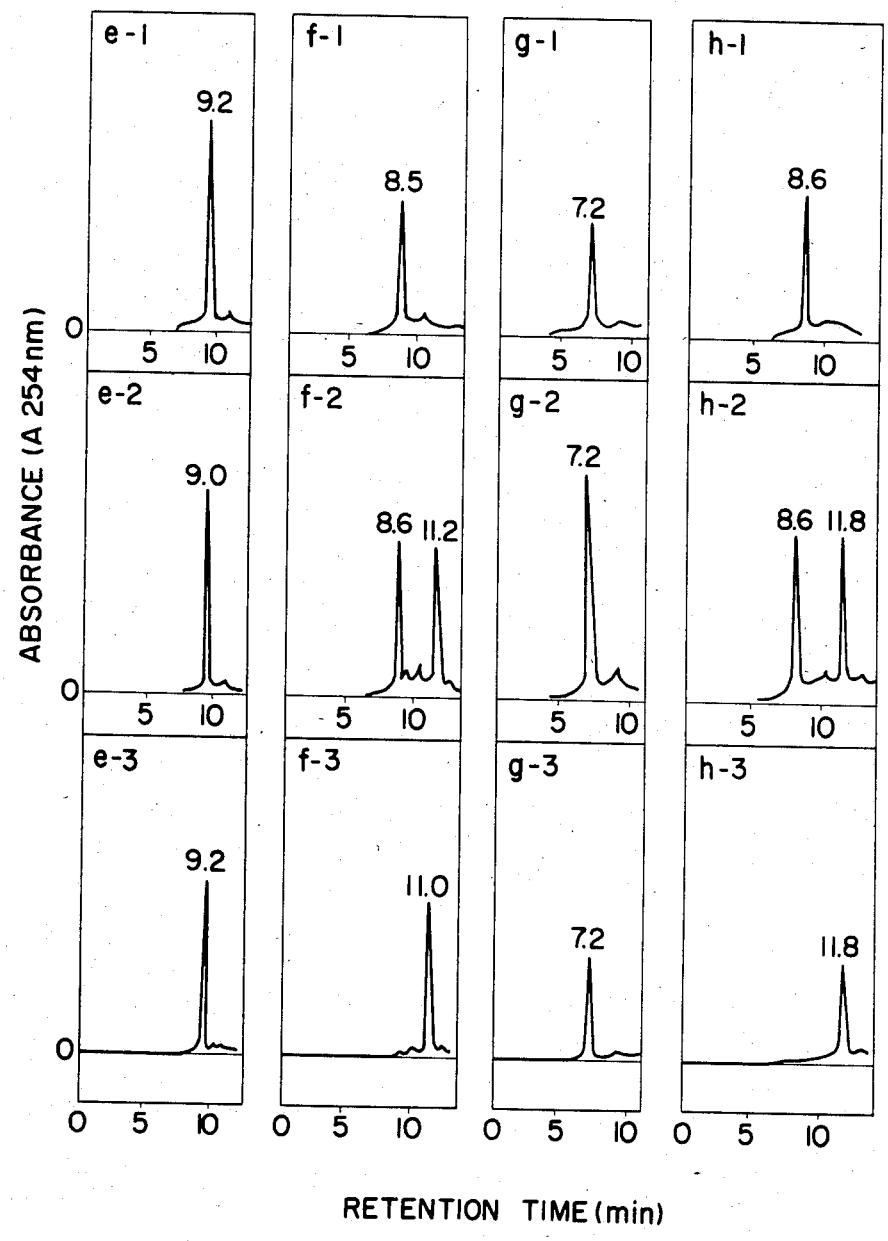
Figure 6:
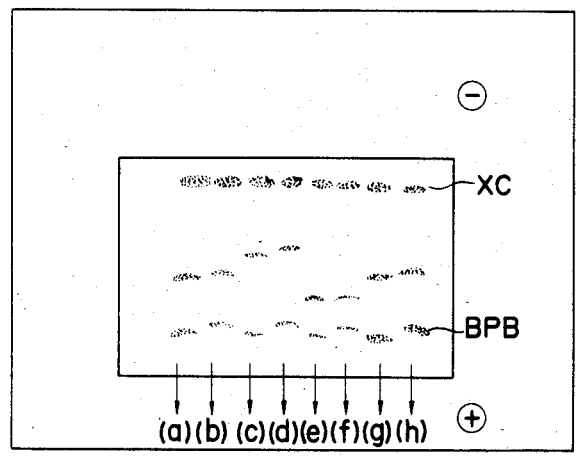
FIGS. 6 and 7 are charts each showing the results of electrophoresis in Example 1.
Figure 7:
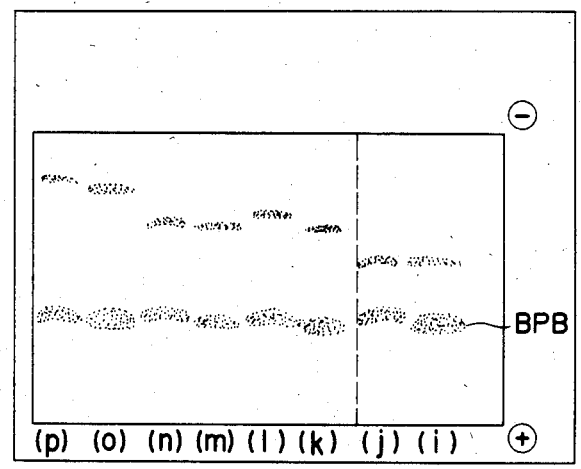

The above results are shown in FIG. 4 and FIG. 5 (results of high-speed liquid chromatography) and in FIG. 6 and FIG. 7 (results of electrophoresis).

FIG. 4 shows elution patterns of high-speed liquid chromatography. In this Figure, each of the numerals 1 shows the chromatogram of the compound before the reaction, each of the numerals 2 that of a mixture of the compounds before and after the reaction, and each of the numerals 3 that of the compound after the reaction with the biotin active ester. (a) is the chromatogram in Experiment 3-1, (b) is the chromatogram in Experiment 2-1, (c) is the chromatogram in Experiment 3-2, and (d) is the chromatogram in Experiment 2-2, respectively. The numerical value on the peak shows the retention time.

FIG. 5 shows elution patterns of high-speed liquid chromatography. In this Figure, each of the numerals 1 shows the chromatogram of the compound before the reaction, each of the numerals 2 that of a mixture of the compounds before and after the reaction, and each of the numerals 3 that of the compound after the reaction with biotin active ester. (e) is the chromatogram in Experiment 3-3, (f) is in Experiment 2-3, (g) is in Experiment 3-4, and (d) is in Experiment 2-4, respectively. The numerical value on the peak shows the retention time.

FIG. 6 shows the results of electrophoresis, in which (a) and (b) show the electrophoresis profile before and after reaction in Experiment 3-1, respectively. Similarly, (c) and (d) show Experiment 2-1, (e) and (f) show Experiment 3-2, (g) and (h) show Experiment 2-2, respectively, with the biotin active ester. XC indicates the band of xylene cyanol and BPB that of bromophenol blue, and both are used as the labels in electrophoresis. In this drawing, the upper side indicates the minus side, and the lower side the plus side.

FIG. 7 shows the results of electrophoresis, in which (i) and (j) show Experiment 3-3, (k) and (l) show Experiment 2-3, (m) and (n) show Experiment 3-4, (p) and (o) show Experiment 2-4, respectively, with the biotin active ester. BPB has the same meaning as mentioned above, and in this drawing, the upper side indicates the minus side, and the lower side the plus side.

As seen from the results of high-speed liquid chromatography (FIG. 4 and FIG. 5), in Experiment 3, the compound having a 5'-hydroxyl group represented by the formula 12 (FIG. 4a-1,3, FIG. 4c-1,3, FIG. 5e-1,3 and FIG. 5g-1,3 did not react with biotin, and gave a peak at the same position before and after reaction. In contrast, in Experiment 2, the oligonucleotide derivative [formula 11] reacted with biotin and yielded a new peak. The peak of the starting material (FIG. 4b-1, FIG. 4d-1, FIG. 5f-1 and FIG. 5h-1) disappeared, and a new peak through the reaction with the biotin active ester was revealed (FIG. 4b-3, FIG. 4d-3, FIG. 5f-3 and FIG. 5h-3). In FIG. 4 to FIG. 5, each of the numerals 2 shows the chromatogram of a mixture of the compounds before and after the reaction. These results clearly suggest that the compounds [(12)] never react with the biotin active ester, and that the compounds [(10)] react quantitatively to give the compounds [(11)].

Then, electrophoresis analysis of the reaction between the 5'-hydroxyl compound [(12)] and the biotin active ester in FIG. 6 and FIG. 7 [see (a)/(b), (e)/(f), (i)/(j) and (m)/(n)] shows that no difference can be seen in the positions of the bands before the reaction [(a), (e), (i) and (m)] and those after the reaction [(b), (f), (j) and (n)]. It can thus be concluded that no reaction with biotin occurred. On the other hand, in the reaction of the oligonucleotide [10] having primary amino group with the biotin active ester [(c)/(d), (g)/(h), (k)/(l) and (o)/(p)] in FIGS. 6 and 7, the positions of the bands before the reaction [(c), (g), (k) and (o)] are different from those after the reaction [(d), (h), (l) and (n)], thus indicating that the reaction with biotin occurred.

From the above results, it can be seen that the compound having primary amino group as prepared above reacts selectively and quantitatively with the biotin active ester.

Example 2 (Preparation of DNP-oligonucleotide)

Flow chart:

The compound of the present invention (the compound [(11)] in the Figure) was produced according to the flow chart in FIG. 2.

The symbols in FIG. 2 are the same as those described in Example 1, except for the following:

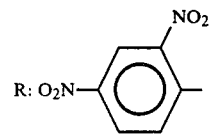

Synthesis of the Compound [VI] ([(10)] In FIG. 2)

Experiment 1-1

The compound [VI] was prepared in the same manner as described in Example 1.

Preparation of 2,4-dinitrophenyl-pentadecaadenylic acid [(11)]

Experiment 2-1

About 1.0 OD of the pentadecaadenylic acid derivative [(10)] synthesized in the above Experiment 1-1 was dissolved in 0.1M sodium bicarbonate solution (pH 8.3), and the reaction was carried out with addition of 5 μl (great excess) of a solution of 1-fluoro-2,4-dinitrobenzene in ethanol (50 mg/ml) at 37° C. for 2 hours. Then, the product was diluted with 30 μl of water and washed four times with 150 μl of ether to obtain 2,4-dinitrophenyl-pentadecaadenylic acid [(11)]. The reaction was monitored by high-speed liquid chromatography.

The compounds [(10)] synthesized in the above Experiments 1-2, 1-3 and 1-4 were also subjected to the same operation as described in Experiment 2-1 to prepare compounds [(11)] corresponding to respective compounds. The experiments conducted here are called Experiments 2-2, 2-3 and 2-4.

The compounds prepared in Experiment 2 are shown in Table 4. This Table is the same as Table 2 in Example 1.

TABLE 4

| | | Derivative Identities of Compound (11) |
|---|---|---|
| Experiment | m + n | $(B)_{m+n}B$ |
| 2-1 | 14 | A A A A A A A A A A A A A A A |
| 2-2 | 14 | T T T T T T T T T T T T T T T |
| 2-3 | 14 | G G A T G C A T C A C C A C C |
| 2-4 | 16 | A A T C T G G T G A G A A G C G C |

In the above Table, A represents adenine, T thymine, G guanine and C cytosine.

Reference Experiment 3

For the purpose of comparison with respect to reactivity, the compounds [(12)] having 5'-hydroxyl group obtained by deprotection of the oligonucleotides [(7)] as prepared above Experiments 1 were also allowed to react in the same manner with 1-fluoro-2,4-dinitrobenzene.

The reference experiments conducted here are called Experiments 3-1, 3-2, 3-3, 3-4. The compounds used in Experiments 3 are shown in Table 5. This Table is the same as Table 3 in Example 1.

TABLE 5

| | | Derivative Identities of Compound (12) |
|---|---|---|
| Experiment | n | $(B)_nB$ |
| 3-1 | 12 | A A A A A A A A A A A A A |
| 3-2 | 12 | T T T T T T T T T T T T T |
| 3-3 | 12 | A T G C A T C A C C A C C |

TABLE 5-continued

| Experiment | n | Derivative Identities of Compound ⑫ (B)ₙB |
|---|---|---|
| 3-4 | 14 | T C T G G T G A G A A G C G C |

In the above Table, A represents adenine, T thymine, G guanine and C cytosine.

Figure 8:
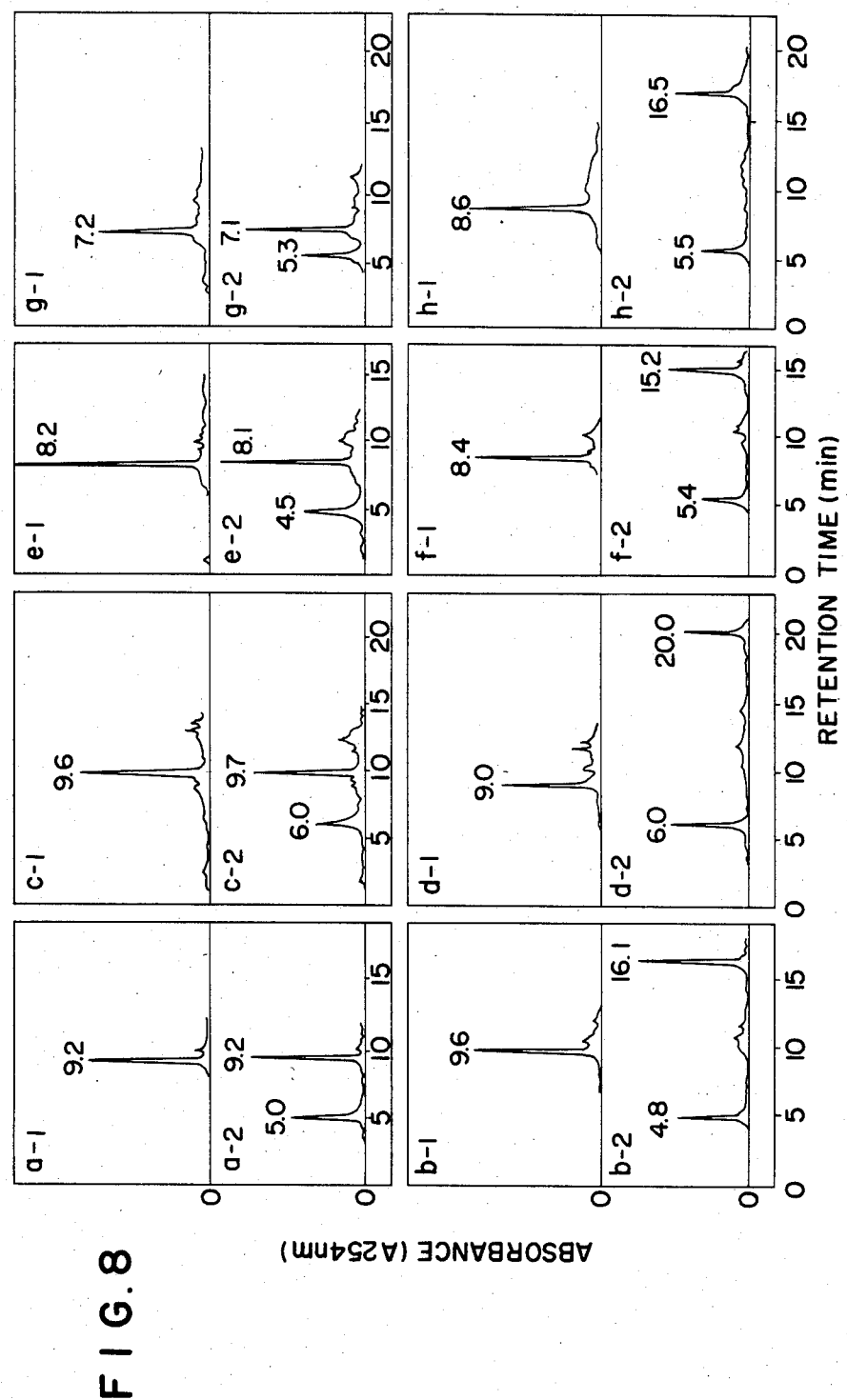
FIG. 8 is a chart showing elution patterns of the high-speed liquid chromatography in Example 2.

The above results are shown in FIG. 8 (results of high-speed liquid chromatography).

FIG. 8 shows elution patterns of high-speed liquid chromatography. In this Figure, each of the numerals 1 indicates the chromatogram of the compound before the reaction, and each of the numerals 2 indicates that of the compound after the reaction with 1-fluoro-2,4-dinitrobenzene. (a) shows the chromatogram in Experiment 3-1, (b) in Experiment 2-1, (c) in Experiment 3-2, (d) in Experiment 2-2, (e) in Experiment 3-3, (f) in Experiment 2-3, (g) in Experiment 3-4, and (h) in Experiment 2-4, respectively. The numerical value on the peak shows the retention time.

As can be seen from these results, the compounds having 5'-hydroxyl group represented by the formula [⑫] (a-1, c-1, e-1 and g-1 in FIG. 8) do not react with 1-fluoro-2,4-dinitrobenzene (a-2, c-2, e-2 and g-2 in FIG. 8).

In contrast, the oligonucleotide derivative [⑩] reacted with 1-fluoro-2,4-dinitrobenzene, and yielded a new peak. The peak of the starting material (b-1, d-1, f-1 and h-1 in FIG. 8) disappeared and a new compound is formed through the reaction (b-2, d-2, f-2 and h-2).

In other words, it can be seen that the compound [⑩] having a primary amino group reacts selectively and quantitatively with 1-fluoro-2,4-dinitrobenzene to give the compound [⑪] and that the compound [⑫] never reacts with it.

Each of the peaks obtained upon elution at a retention time of about 5 minutes in FIG. 8 may be considered to correspond to 2,4-dinitrophenol.

In Examples 1 and 2, high-speed liquid chromatography was conducted by means of HPLC System Tri-Roter III produced by Nippon Bunko under the following measurement conditions:
Column: μ-Bondapak C18 (Waters)
Flow rate: 2 ml/min.
Eluant: 20 mM-TEAA buffer (pH 7.2) containing acetonitrile
Concentration gradient: conc. of acetonitrile 6 to 14%/16 min. (15% after 16 min.)

What is claimed is:

1. A nucleotide comprising an oligonucleotide of the formula

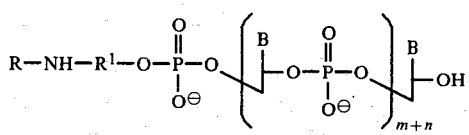

wherein R is

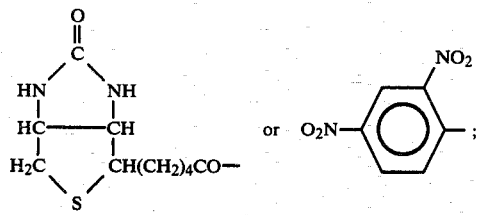

(m+n) is an integer from 1 to 46; $R^1$ is a straight or branched $C_2$-$C_{20}$ alkylene; and each B may be the same or different and is at least one nucleoside residue carrying a base B selected from the group consisting of adenine, cytosine, guanine and thymine.

2. A nucleotide according to claim 1, wherein m is a natural number of 0 to 6, and n is a natural number of 0 to 40.

3. A nucleotide according to claim 1, wherein R is

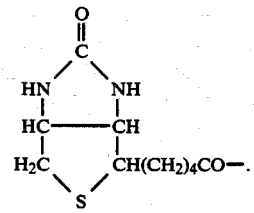

4. A nucleotide according to claim 1, wherein R is

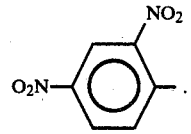

5. The nucleotide of claim 1 wherein m is 1-4 and n is 0-20.

* * * * *